United States Patent [19]

Langley

[11] Patent Number: 5,437,624

[45] Date of Patent: Aug. 1, 1995

[54] SINGLE NEEDLE RECIRCULATION SYSTEM FOR HARVESTING BLOOD COMPONENTS

[75] Inventor: Robert W. Langley, Westminster, Colo.

[73] Assignee: Cobe Laboratories, Inc., Lakewood, Colo.

[21] Appl. No.: 110,432

[22] Filed: Aug. 23, 1993

[51] Int. Cl.[6] .............................................. A61M 37/00
[52] U.S. Cl. ........................................................ 604/4
[58] Field of Search ........................................ 604/4–6

[56] References Cited

U.S. PATENT DOCUMENTS

| | | | |
|---|---|---|---|
| 4,086,924 | 5/1978 | Latham, Jr. | 604/6 |
| 4,094,461 | 6/1978 | Kellogg et al. | 233/40 |
| 4,098,275 | 7/1978 | Consalvo | 604/5 |
| 4,223,672 | 9/1980 | Terman | 604/5 |
| 4,285,464 | 8/1981 | Latham, Jr. | 604/6 |
| 4,643,714 | 2/1987 | Brose | 604/4 |
| 4,648,866 | 3/1987 | Malbrancq et al. | |
| 4,655,742 | 4/1987 | Vantard | |
| 4,687,580 | 8/1987 | Malbrancq et al. | |
| 4,708,712 | 11/1987 | Mulzet | 494/45 |
| 4,991,743 | 2/1991 | Walker | 222/103 |

FOREIGN PATENT DOCUMENTS 4129639  2/1983  Germany .

*Primary Examiner*—Jerome L. Kruter
*Attorney, Agent, or Firm*—Greenlee and Winner

[57] ABSTRACT

A single needle system for withdrawing donated blood, processing the blood to harvest components such as platelets, and returning processed blood to the donor through the single needle. Processing is performed by a centrifuge which separates blood components into stratified layers with a buffy coat containing platelets and white blood cells stably interfacing a red blood cell layer. Blood is withdrawn during a draw cycle and returned to the donor during a return cycle. A recirculation system is provided so that blood flows at a reduced rate through the processing system during the return cycle in order to minimize return cycle time while maintaining the stable position of the interface between buffy coat and red blood cell layers. A storage bag receives processed blood during the draw cycle and blood is squeezed from the bag during the return cycle, a portion returned to the donor and another portion entering the recirculation path. A pressure sensor is located in the return path to indicate an empty storage bag upon a precipitous drop in pressure. In that manner an immediate switch to the draw cycle is made to further minimize return cycle time. To still further minimize the return cycle time, flow resistance in the return path is minimized with more than 80% of the flow resistance in the return path associated with the needle.

43 Claims, 5 Drawing Sheets

STATE TABLE FOR SSN AND SNR

| COMPONENT OR FUNCTION | STARTUP PHASE ||||||| RUN PHASE ||||
|---|---|---|---|---|---|---|---|---|---|---|
| | SSN ($V_{IN} < 320$) || SNR ($V_{IN} < 400$) ||| SSN ($V_{IN} > 320$) || SNR ($V_{IN} > 400$) ||
| | PRIME DIVERT | DRAW CYCLE | RETURN CYCLE | PRIME DIVERT | DRAW CYCLE | RETURN CYCLE | DRAW CYCLE | RETURN CYCLE | DRAW CYCLE | RETURN CYCLE |
| AC PUMP | ON | ON | OFF | ON | ON | OFF | ON | OFF | ON | OFF |
| INLET PUMP | ON | ON | OFF | ON | ON | OFF | ON | OFF | ON | ON |
| COLLECT PUMP | ON | ON | OFF | ON | ON | OFF | ON | OFF | ON | ON |
| PLASMA PUMP | ON | ON | OFF | ON | ON | OFF | ON | OFF | ON | OFF |
| RETURN VALVE | CLOSED | CLOSED | OPEN | CLOSED | CLOSED | OPEN | CLOSED | OPEN | CLOSED | OPEN |
| PLT COLLECT VALVE | CLOSED | OPEN FOR $V_{IN}>200$ | OPEN | CLOSED | OPEN FOR $V_{IN}>300$ | OPEN | OPEN | OPEN | OPEN | OPEN |
| PLASMA COLLECT VALVE | CLOSED | OPEN FOR $V_{IN}>500$ | OPEN | CLOSED | OPEN FOR $V_{IN}>400$ | OPEN | OPEN | OPEN | OPEN | OPEN |
| CYCLE CONTROL | NA | VOLUME | TIME | NA | VOLUME | TIME | VOLUME | TIME | VOLUME | PRESSURE |
| RECIRCULATION FLOW | NO | NO | NO | NO | NO | NO | NO | NO | NO | YES |
| RETURN FLOW TO DONOR | NO | NO | YES | NO | NO | YES | NO | YES | NO | YES |
| RBC LINE HEMATOCRIT | 65% | 65% | | 100% | 65% | | 55% | | FUNCTION OF FLOW | |

FIG. 4

SINGLE NEEDLE RECIRCULATION SYSTEM FOR HARVESTING BLOOD COMPONENTS

SINGLE NEEDLE RECIRCULATION SYSTEM FOR HARVESTING BLOOD COMPONENTS

This invention relates to harvesting blood components from a donor by processing the donated blood and returning it to the donor through the same needle from which it was withdrawn.

BACKGROUND OF THE INVENTION

Donated blood is typically processed by withdrawing it through a needle and sending it through a disposable tubing set to a centrifuge in order to separate the blood into its various components. The centrifugal apparatus is fitted with a disposable plastic vessel through which the blood is circulated. The vessel is fitted into a centrifuge bowl that is driven by a motor. An exemplary vessel is a circumferential separation channel having several outlets positioned at different radial positions within the channel in order to remove blood components separated into stratified layers of differing density by the centrifuge. Red blood cells (RBC), being the most dense of the components, are packed within the channel at the most radially outward location, whereas the stratified layer of plasma is at the most radially inward location. A relatively thin, yellowish layer, called the buffy coat, contains white blood cells and platelets and is located between the red blood cell layer and the plasma layer. Within the buffy coat, the platelets are stratified toward the plasma, while the white blood cells are stratified toward the red blood cells.

U.S. Pat. No. 4,708,712, incorporated herein by reference, describes a two-stage separation channel for collecting platelets separately from white blood cells and also having an outlet for collecting source plasma. The red and white blood cells are returned to the donor, along with most of the plasma.

In a dual-needle procedure, frequently used with a centrifuge apparatus such as described above, whole blood is removed from the donor through a needle usually positioned in one of the donor's arms. The whole blood is then processed by the centrifugal apparatus and the white and red blood cells are returned to the donor through the tubing set and a needle usually positioned in the other arm. If only platelets are being harvested, more of the plasma is returned as well as the red and white blood cells.

For the separation channel described in U.S. Pat. No. 4,708,712, the dual-needle procedure is satisfactory for harvesting platelets in a manner that is relatively free from white blood cell contamination. It is, however, a somewhat difficult procedure for the donor since the donor must remain quiet for a significant period of time with needles in both arms.

In a single-needle process, blood is removed from the donor, processed to collect platelets, and the whole blood, minus the collected platelets and perhaps also minus collected source plasma, is returned to the donor through the same single needle. Platelets are stored in a platelet collection bag, and the plasma is separately collected and stored in a plasma collection bag. Processed blood from which the harvested components have been removed is stored in a separate blood storage return bag during the draw cycle. During the return cycle, a squeezing mechanism places pressure on the external sides of the blood storage bag in order to squeeze the blood from the bag for return to the donor through the single needle. A suitable blood storage bag and pressure mechanism is described in U.S. Pat. No. 4,991,743 which is incorporated herein by reference. In the single-needle process, as originally developed, the flow of blood through the centrifuge is halted for a specific period of time while blood is returned to the donor during the return cycle. As a result, blood flow through the centrifuge is intermittent and the interface between the plasma layer and the red blood cell layer shifts, causing significantly greater contamination of the collected platelets with white blood cells. In addition to greater contamination, the efficiency of collecting a significant percentage of the platelets from the donated blood is considerably less than the efficiency of the dual needle procedure. Thus, while the standard single needle intermittent flow procedure is more comfortable for the donor, it has less desirable results in the collection of platelets.

In order to improve the efficiency of the single-needle procedure and remove the contamination problem, a recirculating loop system has been developed in which the inlet pump is not stopped during the return cycle. Instead, the inlet pump, which pumps whole blood into the separation channel during the draw cycle, continues to operate during the return cycle to recirculate and reprocess blood already in the system. The recirculated blood, together with blood stored in the storage bag, are combined to provide both the recirculation flow to the inlet pump and the return flow to the donor.

In a prior art recirculation system, the draw cycle is operated for a period sufficient to withdraw and process a specific volume of whole blood from the donor. Once that volume has been obtained, the system is switched to a return cycle by opening a valve in the return line and putting pressure on the storage bag. Blood squeezed from the bag is returned in the reverse direction through the needle into the donor until the bag is essentially emptied, at which time the valve is closed and blood is once again drawn from the donor to the inlet pump. In this system, the instantaneous flow of blood to the donor in the return cycle is regulated in order to limit the amount of anticoagulant solution returned to the donor. To accomplish that end, the speed of the inlet pump is reduced during the return cycle and a programmable restriction valve is placed in the return line. In that manner the recirculation flow is related to the re-infusion flow in order to regulate the re-infusion flow to a desired instantaneous level. The time duration of the return cycle is lengthened to accommodate the need to regulate re-infusion flow and also to improve the efficiency of the process since additional platelets are harvested by reprocessing blood in the return cycle. A lengthy return cycle will reprocess more blood for a given recirculation flow.

The current invention seeks to maintain undisturbed the RBC interface of the buffy coat in the centrifuge throughout both the draw and return cycles while minimizing the length of time for the return cycle. It has been determined that it is not necessary to regulate the instantaneous flow of anticoagulant back to the donor as long as the average flow of anticoagulant returned over a complete single needle cycle is kept within the tolerance of the donor. As a consequence, a system has been developed in which the recirculation flow and the re-infusion flow are essentially independent during the return cycle. Instead, the recirculation flow is desirably established at as small a fraction as possible of the inlet flow during the draw cycle in order to minimize the duration of the return cycle and still maintain the stability of the interface. The re-infusion flow is regulated primarily by needle size; no restrictions are placed in the return flow line and the return line flow resistance is deliberately minimized.

By maintaining a stable interface at which the platelets are separated from the blood within the centrifuge, contamination of platelets by white blood cells is reduced to a level that is comparable to or less than that of the double-needle procedure. Platelet collection efficiency is improved by reducing inlet pump speed during the return cycle and thereby achieving an efficiency similar to or above the efficiency of the dual needle procedure.

While the prior art standard single-needle non-recirculation procedure is comfortable for the donor, the previous procedures can be used efficiently with only about 70% of the donor population. Various physiological considerations determine the maximum practical inlet flow rate—the size, the weight, the sex, and the hematocrit (red blood cell content) of the donor are important in determining the maximum practical flow rate for removal of blood from the donor by the inlet pump and for effective processing of blood by the centrifuge. The speed of the pump during the draw cycle is established according to those considerations. Since the total time for the procedure may be approximately an hour and 30 minutes, it is desirable to operate at the maximum practical flow rate for the specific donor. For the largest of donors, that may be about 90 milliliters per minute for the double-needle procedure. However, that flow rate corresponds to an average blood processing rate of only about 50 milliliters per minute for the standard non-recirculating single-needle procedure. The ratio, 5/9, is approximately the ratio of the duration of the draw cycle to the total cycle time for draw and return. As mentioned above, a prior art single-needle recirculating procedure desires long return cycles of perhaps even greater duration than 5/9 in order to control the return of anticoagulant. In this invention, it is desired to minimize the return cycle time in order to improve the average blood processing rate for a given inlet pump flow rate and thereby minimize the length of time for a completed donation.

With the return cycle duration minimized, a lower instantaneous flow rate during the draw cycle is possible for the same blood processing rate. Two additional benefits are achieved thereby: (1) when the instantaneous flow rate is lowered, the cell separation efficiency of the separation channel is increased thereby providing better separation and improved harvesting of the platelets; and (2) as the instantaneous flow rate is decreased, the percentage of the donor population which can be efficiently accommodated by the single-needle procedure is increased to about 98% of the donor population, thus providing the benefits of the single needle system to many more people.

SUMMARY OF THE INVENTION

Briefly stated, the invention achieves the minimization of return cycle time by lowering the speed of the inlet pump during the return cycle, by minimizing flow resistance in the return path, and by instituting a volume/pressure control system. A pressure gauge is placed in the return line and, as blood is squeezed into the return line from the storage bag, pressure is maintained in the return line at a relatively high level. However, as soon as the bag is emptied, the pressure in the return line drops precipitously, indicating that the bag is empty. At that point the system is switched back to a draw cycle.

Another aspect of the invention is to limit the maximum allowable plasma fraction that can be collected in accordance with the blood processing rate. During the collection of plasma, the recirculation system of the invention requires the recirculation of high-hematocrit blood. Because the separation channel processing efficiency is lowered for high-hematocrit blood, the target hematocrit level in the packed red blood cell (RBC) return line and the allowable plasma collection fraction, are designed as a decreasing function as the blood processing rate increases rather than a constant target and fraction that are independent of the blood processing rate.

During the start-up phase of the procedure, for a system that is primed with saline, blood displaces the saline that was used to prime and displace air from the tubing set. To minimize the time needed for the start-up phase, recirculation is not performed during the return cycle because the recirculation of saline in the tubing set prolongs the start-up and delays the beginning of platelet collection. For a system that is primed with blood, recirculation can begin as soon as the tubing set is filled with blood.

BRIEF DESCRIPTION OF THE DRAWINGS

The above-mentioned and other features and objects of the invention and the manner of attaining them will become more apparent and the invention itself will best be understood by reference to the following description of embodiments of the invention taken in conjunction with the accompanying drawings, a brief description of which follows.

FIG. 4 shows a state table for the start-up phase and the run phase of the recirculating system of the embodiment of FIG. 1.

FIG. 5A shows the protocol for a standard single needle system while FIG. 5B shows the protocol for the single needle recirculation system of the embodiment of FIG. 1.

DETAILED DESCRIPTION

Figure 1:
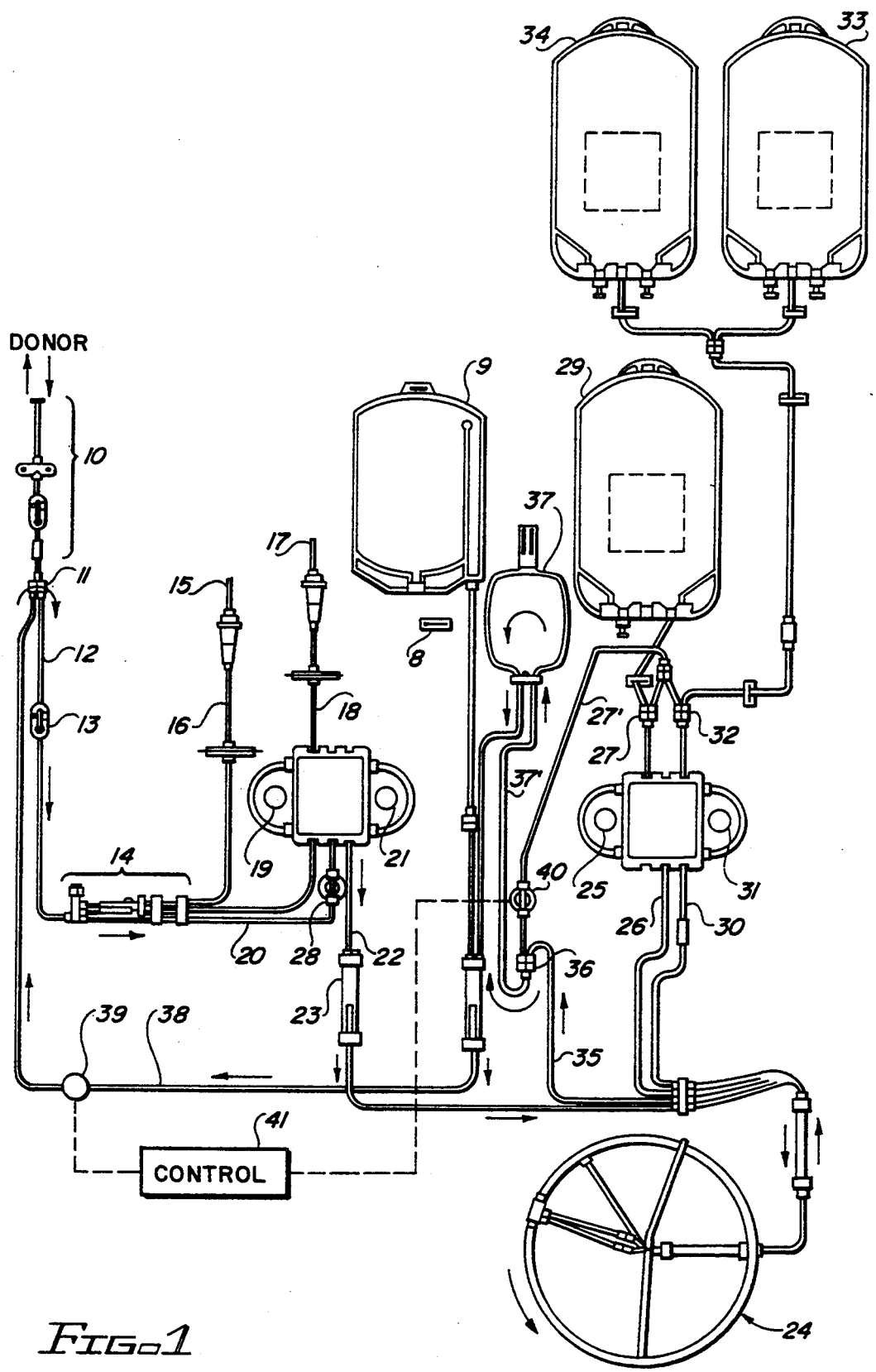
FIG. 1 is a diagram of the recirculation flow in an embodiment of the single-needle recirculation system of the invention.

Referring now to the drawing, like numbers indicate like features and the same number appearing in more than one figure refers to the same element.

FIG. 1 shows the recirculation flow within an exemplary system embodying the invention. A single lumen needle 10 is inserted into a donor for obtaining platelets or both plasma and platelets from the blood of the donor. The needle is connected to a first branch of a Y connector 11. A second branch of the Y connector is connected to the inlet line 12 which passes through a line clamp 13 to a manifold 14. A connector 15 is attached to a saline bag (not shown) for introduction of saline liquid through line 16 to manifold 14. A connector 17 is attached to an anti-coagulant bag (not shown) for introduction of anti-coagulant solution through line be to anti-coagulant pump 19. The outlet of pump 19 is connected to the manifold 14 for insertion of a controlled amount of anti-coagulant solution to blood drawn from the donor. It is desirable to minimize the distance between manifold 14 and the single needle 10 in order that the anti-coagulant solution can be mixed with the donor's blood as soon as possible in the tubing set of the recirculation system. Blood from manifold 14 is presented to the inlet side of inlet pump 21 through line 20 and access pressure sensor 28. The outlet side of inlet pump 21 is connected through line 22 and a drip chamber 23 to at least one separation vessel. In this exemplary embodiment, the separation vessel is a separation channel 24.

As discussed above, plastic separation channel 24 is inserted into the bowl of a centrifuge for separating out the various components of the blood. Plasma is drawn out of the separation channel by the plasma pump 25 over the plasma collect line 26. The plasma is passed through a Y connector 27 and is either sent to blood storage bag 37 via lines 27' and 37' or is collected in plasma collect bag 29. Platelets are drawn from the separation channel 24 over line 30 to the collect pump 31 and are pumped through Y connector 32 into one or the other of platelet collect bags 33 and 34. Valves or tube clamps, not shown, control the direction of flow through Y connectors 27 and 32.

High-hematocrit blood is drawn from the separation channel through line 35, Y connector 36, and line 37' to the storage bag 37. If source plasma is not collected, the plasma in line 27' is combined with the blood in line 35 for storage in bag 37. The return line 38 runs from the storage bag 37 through the return valve 39 to a third branch of the Y connector 11.

During a draw cycle, the return valve 39 is closed so that the processed blood is accumulated in the storage bag 37. Platelets are collected in the platelet collect bags 33 and 34 and, if desired, plasma is collected in the bag 29. If it is not desired to collect plasma, the plasma is directed to the storage bag 37.

During the return cycle, the return valve 39 is opened and pressure is exerted on the storage bag 37 to squeeze blood therefrom through line 38 to the Y connector 11 and from there through the needle 10 to the donor. A portion of the blood in return line 38 is passed through Y connector 11 to the inlet line 12 for presentation to the inlet pump 21. In that manner, inlet pump 21 continues to provide a flow of blood into the separation channel 24, whether in the draw cycle or in the return cycle. By maintaining the flow of blood to the separation channel, the interface position between the various blood components in the channel is not disturbed when changing from draw cycle to return cycle. By not disturbing the interface, contamination of the platelet collection line with white blood cells is minimized.

During the return cycle, a constant volume of blood remains in the recirculating system which extends from inlet line 12 through the separation channel, out of the channel through lines 35 and 37' into the storage bag 37, out of bag 37 through the return line 38 and Y connector 11 back to inlet line 12. Platelets continue to be collected over line 30, but the volume so collected is made up from the return bag 37. The blood being reprocessed in the centrifuge 24 during the return cycle is mixed with the blood in storage bag 37 for presentation to the return line 38. By reprocessing a portion of the blood stored in bag 37, additional platelets not previously removed from the processed blood are collected, thus providing an improvement in the efficiency of platelet collection.

A return pressure sensor 40 located in return line 27' senses the pressure being exerted on the fluid in bag 37. Sensor 40 can be located at any convenient place in the return system such as in line 38 or associated with storage bag 37. Once the bag 37 is emptied, the sensor 40 shows a sudden drop in pressure signalling that the bag 37 is empty and that the return cycle can be terminated and the draw cycle begun again. The pressure sensor 40 is connected to a microprocessor-based control system 41 for switching return valve 39 to a closed position and resuming the draw cycle as soon as the sudden drop in pressure is sensed.

As mentioned above, two of the significant advantages of the invention are minimizing instantaneous flow rates in order to accommodate a greater percentage of the donor population with the single needle procedure and minimizing the length of time for the donor to be attached to the system. The minimizing of return cycle time accomplishes these ends and is furthered by utilizing the pressure sensing approach. It is also valuable to increase the size of the tubing set in the return path relative to the remainder of the tubing set in order to minimize the resistance to the flow of blood through the return path. That is to say, if the total return flow resistance in the return path includes the flow resistance through the needle, summed with the flow resistance through the remainder of the return path, i.e., the flow resistance associated with the storage bag 37, the flow resistance associated with the Y connector 11, and the flow resistance of the return line 38, it is desirable to provide 80% or more of the total return flow resistance in the needle. In that manner, the return cycle duration is minimized, thus achieving a lower instantaneous flow rate for the same blood processing rate.

Lowering the flow rate of blood through the recirculating system also reduces the duration of the return cycle. To minimize return cycle time, it is desirable to reduce the recirculated flow as low as possible while still maintaining the stability of the interface position between the RBC and the buffy coat. Maintaining stability keeps collected platelet purity high. A low recirculated flow rate improves the efficiency of collecting platelets from the donated blood as well as minimizing return cycle time.

While the volume of blood in the recirculation path does not change with flow rate, the spring actuated flow controller which squeezes blood from the storage bag must overcome the resistance of the return line to recirculate blood to the inlet pump. By keeping the recirculated flow rate low, a lower percentage of the spring force is used for recirculation leaving a higher percentage of spring force available for returning blood to the donor. In that manner, return cycle duration is minimized by a low recirculation flow rate.

It should be noted, as stated above, that it is valuable to increase the size of the tubing in the return path in order to minimize the resistance to the flow of blood through the return path. As the resistance of the return path approaches zero, the effect of recirculation flow rates on the return cycle duration also approaches zero, thus optimizing the return cycle duration. However, as noted above, even if the effect of recirculation flow rate on the duration of the return cycle were minimized, a low recirculation flow rate is still desirable to keep platelet collection efficiency high. While theoretically a higher recirculation flow rate would reprocess more blood and thereby obtain more platelets, a buffy coat must be stably maintained to keep platelet collection efficiency high. Since the plasma pump is off during the return cycle, a much greater fraction of the separated plasma is forced out the RBC return line. This adversely affects the flow pattern in the separation channel and has the effect of depleting the buffy coat. Therefore a high recirculation flow rate tends to deplete the buffy coat and thereby reduce platelet collection efficiency. Since recirculated blood is high hematocrit blood, there is also the danger of RBC spillover into the platelet collection bag.

To summarize, in order to gain the optimal system for realizing the many benefits of a single needle recirculation system, it is desirable to minimize return cycle duration. That is accomplished by reducing the flow resistance of the return path, by using a volume/pressure control, and by lowering the recirculation flow rate while still maintaining a stable interface of stratified layers in the separation channel of the centrifuge.

When priming the system shown in FIG. 1, saline solution is drawn from a saline bag (not shown) through inlet 15 into the manifold 14. From there, inlet pump 21 pumps the solution throughout the lines and bags of the system so that air is removed. During the start-up phase, as blood enters the system the saline solution is directed to the waste bag 9 until a sensor 8 detects the presence of blood in the entry line to bag 9. At that time the system is switched to return fluid to the donor rather than continuing the flow into the waste bag 9. Collection of blood components, however, does not commence until the system is essentially free of saline solution. At that point, the start-up phase ends and the recirculating collection phase begins.

Figure 2:
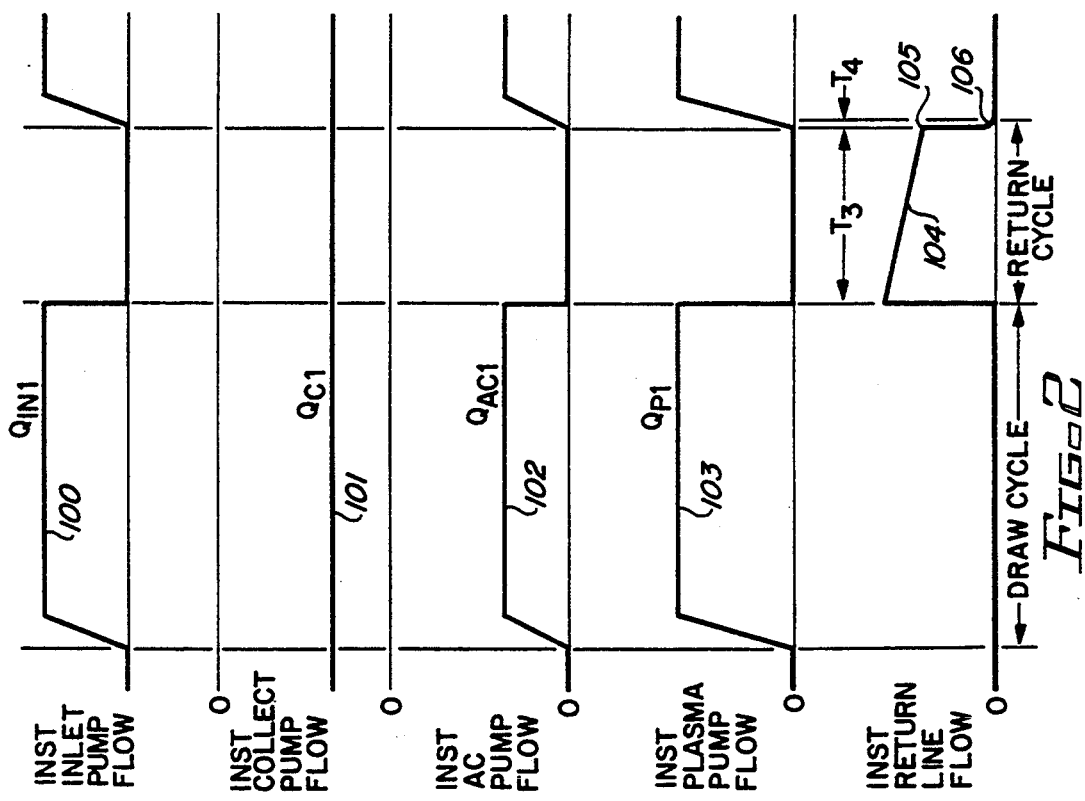
FIG. 2 shows flow profiles within the draw and return cycles for the embodiment of FIG. 1.

FIG. 2 is a diagram of preferred flow profiles within each cycle of the recirculating single-needle procedure according to the invention. Inlet flow 100 is shown as advancing to a steady state, constant profile throughout the draw cycle and dropping to a lower steady state condition during the return cycle. It has been found that when the inlet pump is operated during the return cycle at about one-half the draw cycle speed, the RBC interface is maintained and platelet collection efficiency is improved. The RBC interface can be maintained at greater inlet pump speeds during the return cycle, but platelet collection efficiency is not as good as at lowered speeds. If the inlet pump speed is either too great or too small during the return cycle, the RBC interface will be disturbed and, at excessively high speeds, the buffy coat will be depleted.

For definition, the term platelet collection efficiency is the number of platelets collected divided by the number of platelets processed during the collection period. To derive these values, a blood sample is taken before donation begins for laboratory analysis of the number of platelets per milliliter. The volume of blood drawn and processed from the donor is known, thus enabling a calculation of the total number of platelets processed. A sample of collected platelets is analyzed to determine the total number of platelets collected. In that manner, the values for obtaining platelet collection efficiency are determined.

Profile 101 shows that the flow through the collect pump is also a constant value throughout the draw and return cycles, showing that platelets are collected during both cycles.

Flow profile 102 shows that the flow of anti-coagulant during the draw cycle is halted during the return cycle. Flow profile 103 shows that the plasma flow is also halted during the return cycle.

Figure 3:
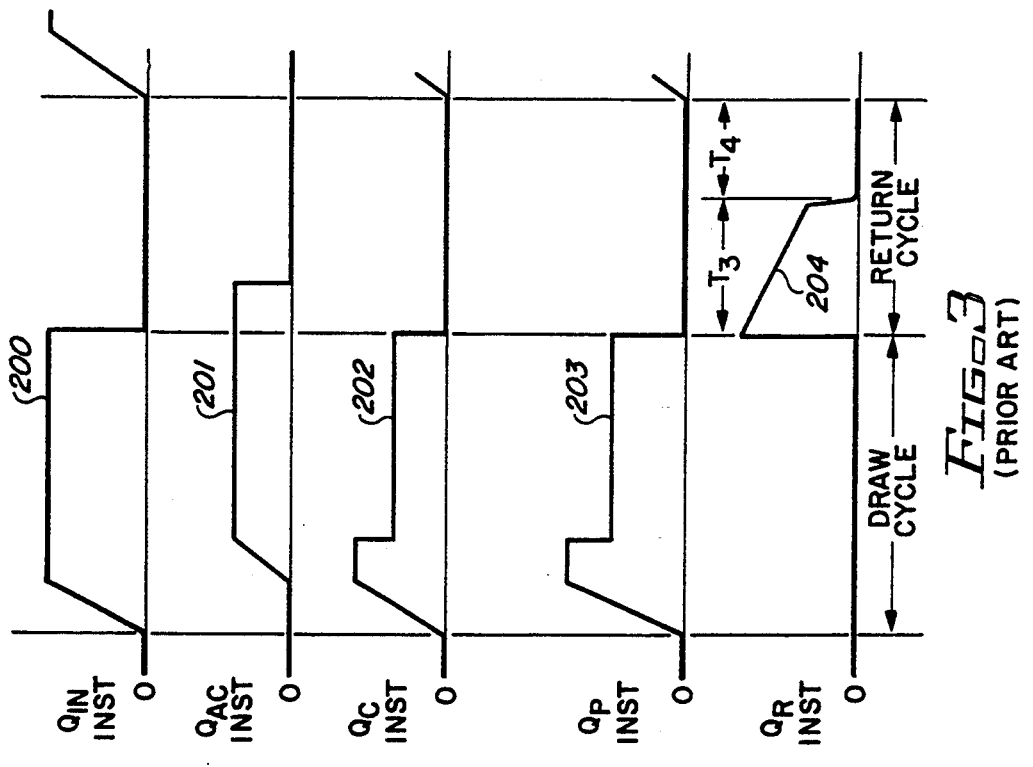
FIG. 3 shows the flow profiles for the previous volume/time standard single needle system with no recirculation.

Flow profile 104 shows the return flow in line 38. The sloping linear portion of flow profile 104 during the return cycle represents the return flow occurring during the period in which pressure is placed on the flexible storage bag 37 to squeeze blood from the bag into the return line. At the knee 105 the return flow suddenly drops off, indicating that the bag is substantially empty and that the return cycle can end. At 106 the pressure sensing device 40 triggers the end of the return cycle, and the beginning of the next following draw cycle. Flow profile 104 shows a time period, $T_4$, together with a time period, $T_3$, making up the return cycle with time period $T_4$ approaching zero. In the prior art, volume/time single needle process, the return cycle was established for a specific amount of time, $T_3$ plus $T_4$ where the time period $T_4$ was kept at a substantial value in order to make sure that the storage bag 37 was emptied prior to beginning the draw cycle again. FIG. 3 illustrates $T_3$ and $T_4$ in the standard non-recirculating single needle process which used a specific time for the return cycle. Should some amount of blood continually remain in bag 37 from cycle to cycle and build up from cycle to cycle, the capacity of the bag could be exceeded before the entire procedure ended. Consequently, a relatively long return cycle was needed in order to make sure that the bag was emptied. In the volume/pressure procedure of this invention, a pressure sensor is used to determine when the bag is empty and that it is safe to resume the draw cycle. In that manner, the dead time, $T_4$, is minimized or eliminated thus reducing return cycle time.

As mentioned above, FIG. 3 shows flow profiles within the prior art standard single-needle approach in which there was no recirculation during the return cycle. Instead, the bag 37 was filled during a draw cycle and emptied during a return cycle without the recirculation of blood through the inlet pump and centrifuge. The flow through the inlet pump and centrifuge is shown with flow profile 200, the anti-coagulant flow is shown with profile 201, the collect flow with profile 202, and the plasma flow with profile 203. Note that the inlet flow falls to zero during the return cycle, as does the anti-coagulant flow, the collect flow and the plasma flow. The return flow profile 204 is similar to the return flow profile 104 shown in FIG. 2, except that a significant dead time period, $T_4$, is needed to provide a safety factor for emptying the storage bag, as discussed above.

FIG. 4 shows a state table for an embodiment of the prior art standard single-needle (SSN) intermittent flow process for comparison with the state table for an embodiment of the single-needle recirculation (SNR) constant flow process of the invention. Note that there are three periods during the start-up phase: the prime divert cycle, the draw cycle, and a return cycle. The prime divert period is that period in which the saline solution is diverted into the waste bag 9. The volume of blood processed in the start-up phase is empirically determined and is designed to rid the system of any saline solution which might have mixed with blood prior to beginning the run phase in which platelets and plasma are collected. The chart shown in FIG. 4 shows that the start-up phase for single-needle recirculation is the same as for the standard single-needle intermittent flow procedure; that is, there is no recirculation during the start-up phase. The reason is that if blood is recirculated with a saline component, the start-up phase would lengthen and thereby delay entry of the system into the collect phase. Actually, as may be seen from the state table for the platelet collect valve, the platelets may be collected prior to entry into the collect phase; however, plasma is not collected until essentially all saline is removed. In the SSN procedure, the start-up phase runs for 320 milliliters volume, while in the recirculation procedure the start-up phase continues for 400 milliliters before switching to the run phase. However, plasma collect begins at 400 ml in SNR while it must wait for 500 ml in SSN.

Note that during the initial part of the start-up phase the target hematocrit in the RBC line is 100% in the SNR procedure. The meaning of a 100% hematocrit target is that the combined flow of the plasma pump and collect pump is equal to the inlet plasma flow plus the anti-coagulant flow. As a consequence, most of the red blood cells accumulate in the separation channel during the prime divert period.

During the run phase, the collect pump and the inlet pump remain on during the return cycle providing a stable, steady state RBC interface for the separation channel whether in the draw cycle or the return cycle. Note also that during the run phase the hematocrit target is a function of the inlet flow rate in the SNR process with the flow rate being determined by the size, weight, sex and hematocrit of the donor. The hematocrit target is designed to be a linear function of inlet flow rate, decreasing as the flow rate increases. By relating the hematocrit target to flow rate, the volume of plasma available for collection is maximized without contamination from red blood cells. Basically, the relationship is $C_1-C_2Q_{IN}$ where the constants are determined by the physical parameters of the system.

The capability of a centrifugal separator to separate blood components is limited by its design. Thus, the fraction of the processed plasma that can be separated generally decreases as inlet flow increases, especially for a speed-limited centrifuge. The recirculation of high hematocrit blood exacerbates this limitation. The maximum hematocrit target reflects this limitation and is chosen to maximize the volume of separated plasma available for collection without risking RBC contamination by attempting to remove from the separation channel more plasma than is separated from the processed blood.

Figure 5A:
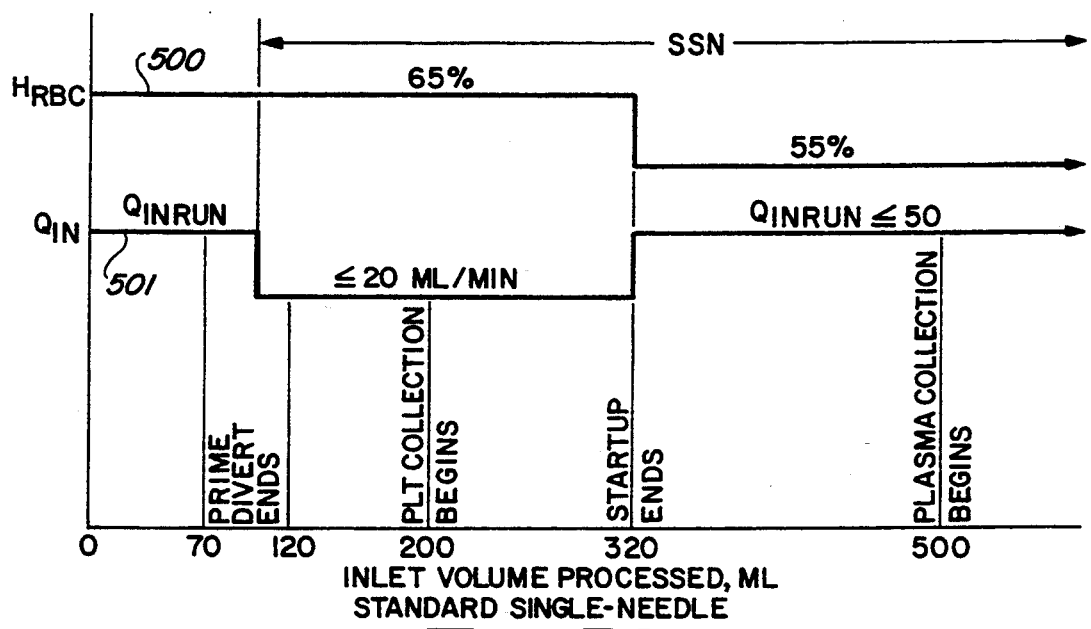
FIGS. 5A and 5B are illustrations of start-up protocol.

FIG. 5A illustrates the hematocrit target 500 during the start-up phase and the run phase of the SSN process for a particular centrifugal separator. FIG. 5A also shows the average flow profile 501 in the inlet pump and separation channel during the start-up phase and the run phase. Note that while platelet collection can begin after processing 200 milliliters during the start-up cycle, the plasma collection does not begin until 500 milliliters have been processed.

Figure 5B:
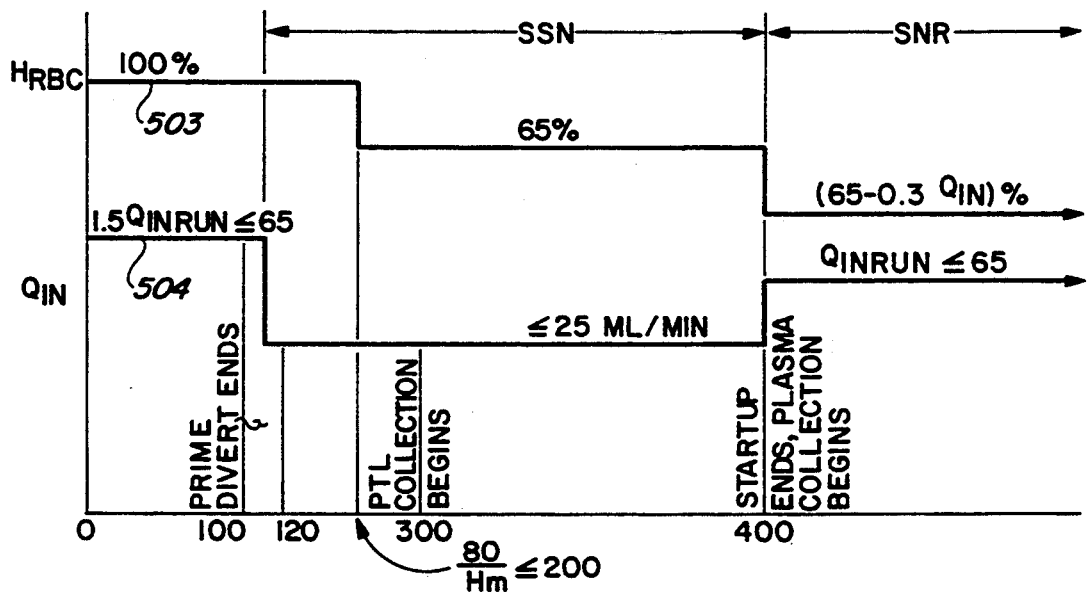

FIG. 5B for the same centrifugal separator shows the single-needle recirculation process of the invention with the target hematocrit levels shown by profile 503. The flow profile for the inlet pump and separation channel is shown by profile 504. In the centrifugal system utilized in FIG. 5B, the target hematocrit during the run phase is related to the inlet flow, $Q_{IN}$, according to the relationship $(65-0.3Q_{IN})\%$.

Figure 6:
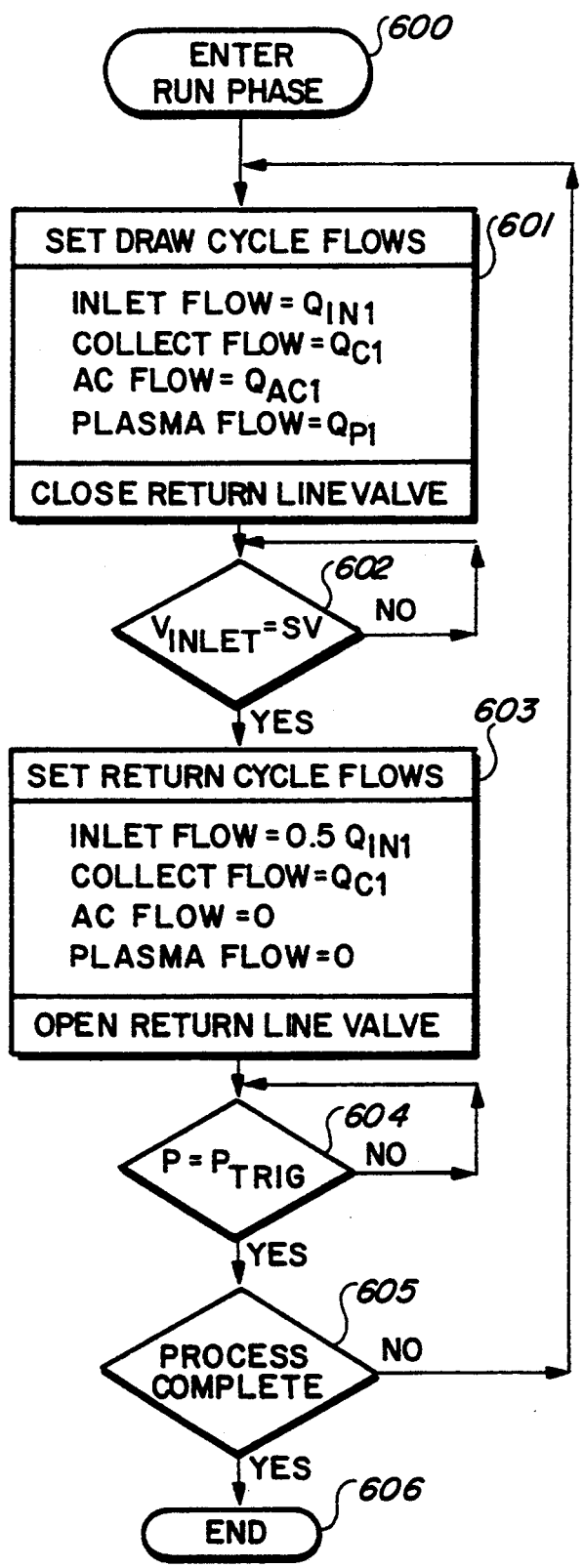
FIG. 6 is a flowchart of the control system used with the embodiment of FIG. 1.

FIG. 6 illustrates the control operation for the embodiment of FIG. 1 performed by the microprocessor-based control device 41 during the run phase. The control operation of FIG. 6 may be performed by any suitable control mechanism, but easily changeable control devices such as a programmable microprocessor are advantageous for optimizing system performance.

Upon completing the start-up phase and entering the run phase 600, the control device 41 at step 601 directs the establishment of draw cycle flows as illustrated in FIG. 2 and FIG. 6. That is, the inlet pump speed is regulated to produce the desired instantaneous steady-state inlet flow, $Q_{IN1}$. The collect pump speed is regulated to produce the desired steady-state collect platelet flow, $Q_{C1}$. The anti-coagulant (AC) pump is regulated to produce the desired steady-state anti-coagulant flow, $Q_{AC1}$. The plasma pump is regulated to produce the desired steady-state plasma flow, $Q_{P1}$. All pumps are conveniently regulated to ramp to the desired steady-state level at the same rate.

Also, upon entering a draw cycle at step 601, the control device issues a signal to close the return line by closing the return valve 39.

During the draw cycle, the control device 41 continually checks the volume of fluid pumped by the inlet pump to determine if it equals the desired stroke volume SV, at step 602. When the desired draw volume, $V_{INLET}$, has been pumped, $V_{INLET}$ equals SV, and the control device 41 issues signals to end the draw cycle and commence the return cycle. These signals are produced at step 603 and include a signal to open the return line valve 39, a signal to set the inlet flow, $Q_{IN2}$, at one-half $Q_{IN1}$, signals to drop the AC flow and the plasma flow to zero, and maintaining the signal to keep the collect flow at the same steady-state level that existed on the draw cycle.

During the return cycle, control device 41 continually checks at step 604 for a signal from pressure sensor 40. When the signal, $P_{TRIGGER}$, arrives, it indicates a detection of a precipitous drop in pressure in return line 38, thereby indicating an empty storage bag 37. Control device 41 then checks at step 605 to determine whether a desired total inlet volume has been processed over a multitude of draw cycles to determine whether processing of the donor's blood is complete. If it is, control device 41 directs entry at step 606 into a shut-down operation to halt the machine; otherwise, return is made to repeat step 601 and begin another draw cycle.

While the invention has been shown and described with respect to the specific embodiments, it is to be understood that the invention can be incorporated into other environments. Also, changes in form and detail may be made without departing from the spirit and scope of the invention.

What is claimed is:

1. A system for separating and collecting blood components during both a draw cycle and a return cycle, said system for drawing and returning blood to a donor through a single lumen needle, comprising
    a connector having at least three branches, a first branch connected to said single lumen needle;
    a constant volumetric flow rate inlet pump with an inlet and an outlet;
    an inlet line connected to a second branch of said connector and to said inlet pump for supplying blood to the inlet side of said pump;
    a centrifuge apparatus with a separation vessel connected to the outlet side of said inlet pump for separating blood components into stratified layers within said vessel;

a collection bag connected to said separation channel for receiving and holding a collected component of the donated blood;

a return path including a return line connected to a third branch of said connector;

a flexible storage bag with an inlet connected to said separation vessel for receiving and holding the processed donated blood other than collected components, said storage bag having an outlet connected to said return line;

a pressure application member in communication with said flexible storage bag for applying pressure to the external sides of said storage bag during said return cycle to force the accumulated fluids in said storage bag into said return line;

a return valve in fluid communication with said return line to open said return line during said return cycle to allow a first portion of said accumulated fluids to be returned to said donor, a second portion of said accumulated fluids passing through said connector to said inlet line for establishing and maintaining a recirculation path for blood during said return cycle;

a sensing device in communication with said return path for producing a signal upon detecting an empty storage bag;

a control device connected to said sensing device, said return valve and said inlet pump, said control device including means for minimizing the time duration of said return cycle.

2. The system of claim 1 wherein said means for minimizing the time duration of said return cycle includes interface control means for establishing the volumetric flow rate of said second portion at a value sufficient to stably maintain the interface position of said stratified layers.

3. The system of claim 2 wherein said interface control means includes means for setting the recirculation volumetric flow rate of said inlet pump on said return cycle substantially lower than the draw volumetric flow rate established during said draw cycle.

4. The system of claim 3 wherein said recirculation flow rate approaches a minimum value sufficient to stably maintain said interface position.

5. The system of claim 4 wherein said recirculation flow rate is 50% or less of said draw flow rate.

6. The system of claim 4 wherein said means for minimizing the time duration of said return cycle further includes
means for closing said return valve thereby ending said return cycle upon receiving said signal detecting an empty storage bag.

7. The system of claim 6 wherein said sensing device monitors pressure in said return path and detects an empty storage bag by a precipitous drop in pressure.

8. The system of claim 6 wherein said means for minimizing the duration of said return cycle further includes said return path wherein the resistance to the flow of blood through the return path is minimal, except for the flow resistance of said needle, said return path including said needle, said connector, said return line, and said storage bag.

9. The system of claim 8 wherein said return line is of a larger diameter than other tubing in said system.

10. The system of claim 8 in which the flow resistance of said needle is more than 80% of the total flow resistance in the return path.

11. The system of claim 10 wherein the target hematocrit level is decreased as a percentage of inlet flow as inlet flow increases.

12. The system of claim 11 wherein the relationship of said target to inlet flow, $Q_{IN}$, is $C_1 - C_2 Q_{IN}$, where $C_1$ and $C_2$ are constant values.

13. The system of claim 6 wherein the relationship of said target to inlet flow, $Q_{IN}$, is $C_1 - C_2 Q_{IN}$, where $C_1$ and $C_2$ are constant values.

14. The system of claim 6 wherein the target hematocrit level is decreased as a percentage of inlet flow as inlet flow increases.

15. The system of claim 14 wherein the relationship of said target to inlet flow, $Q_{IN}$, is $C_1 - C_2 Q_{IN}$, where $C_1$ and $C_2$ are constant values.

16. The system of claim 4 wherein the target hematocrit level is decreased as a percentage of inlet flow as inlet flow increases.

17. The system of claim 16 wherein the relationship of said target to inlet flow, $Q_{IN}$, is $C_1 - C_2 Q_{IN}$, where $C_1$ and $C_2$ are constant values.

18. The system of claim 1 wherein said means for minimizing the time duration of said return cycle includes
means for closing said return valve thereby ending said return cycle upon receiving said signal detecting an empty storage bag.

19. The system of claim 11 wherein said sensing device monitors pressure in said return path and detects an empty storage bag by a precipitous drop in pressure.

20. The system of claim 19 wherein said means for minimizing the duration of said return cycle further includes said return path wherein the resistance to the flow of blood through the return path is minimal, except for the flow resistance of said needle, said return path including said needle, said connector, said return line, and said storage bag.

21. The system of claim 20 wherein said return line is of a larger diameter than other tubing in said system.

22. The system of claim 20 in which the flow resistance of said needle is more than 80% of the total flow resistance in the return path.

23. The system of claim 11 wherein the target hematocrit level is decreased as a percentage of inlet flow as inlet flow increases.

24. The system of claim 23 wherein the relationship of said target to inlet flow, $Q_{IN}$, is $C_1 - C_2 Q_{IN}$, where $C_1$ and $C_2$ are constant values.

25. The system of claim 1 wherein said means for minimizing the duration of said return cycle includes
return path means wherein the resistance to the flow of blood through the return path is minimal, except for the flow resistance of said needle, said return path including said needle, said connector, said return line, and said storage bag.

26. The system of claim 16 wherein said return line is of a larger diameter than other tubing in said system.

27. The system of claim 16 in which the flow resistance of said needle is more than 80% of the total flow resistance in the return path.

28. The system of claim 27 wherein the target hematocrit level is decreased as a percentage of inlet flow as inlet flow increases.

29. The system of claim 28 wherein the relationship of said target to inlet flow, $Q_{IN}$, is $C_1 - C_2 Q_{IN}$, where $C_1$ and $C_2$ are constant values.

30. The system of claim 1 wherein the target hematocrit level is decreased as a percentage of inlet flow as inlet flow Increases.

31. A method of separating and collecting blood components during both a draw cycle and a return cycle of a run phase, said method for drawing and returning blood to a donor through a single lumen needle, said method comprising the steps of:
providing a single lumen needle for insertion into the vein of a donor;
providing a connector having at least three branches, a first branch connected to said needle;
providing an inlet pump with an inlet and an outlet;
providing an inlet line connected to a second branch of said connector and to said inlet pump for supplying blood to the inlet side of said pump;
providing a centrifuge apparatus with a separation vessel connected to the outlet side of said pump, said vessel for separating blood components into stratified layers;
providing a collection bag connected to said separation vessel for receiving and holding a collected component of the donated blood;
providing a flexible storage bag with an inlet connected to said separation vessel for receiving and holding the processed donated blood other than the collected components, said storage bag having an outlet;
providing a return system including said storage bag and a return line connected to a third branch of said connector and to said outlet of said storage bag;
providing a pressure application member in communication with said return bag for applying pressure on the external sides of said return bag during said return cycle to force the fluids in said bag into said return line;
providing a sensing device in communication with said return system;
providing a return valve in fluid communication with said return line;
providing a control device for operating said return valve to close said valve during said draw cycle so that blood enters said inlet pump from said donor, is processed by said centrifuge to harvest blood components, and to send the processed blood to said storage bag, said control device operating said return valve to open said valve during a return cycle so that blood in said storage bag is squeezed into said return line, a first portion of blood in said return line passing through the first branch of said connector to said needle for return to the donor, a second portion of blood in said return line passing through the second branch of said connector to the inlet side of said pump for maintaining circulation of blood through said centrifuge apparatus to said storage bag and return line thereby providing a recirculation flow for reprocessing that portion of the blood not returned to the donor during the return cycle, said control device for minimizing return cycle time by reclosing said return valve thereby ending said return cycle and reinstituting said draw cycle when said sensing device indicates that said storage bag is empty, and
further minimizing return cycle time by providing return line flow resistance at a low level that produces return flow through said needle at a rate that is essentially independent of said recirculation flow.

32. The method of claim 31 wherein the return system flow resistance, excluding flow resistance through said needle, is less than 20% of all flow resistance in said return system, said return system including flow resistance through said storage bag, said return line, said connector, and said needle.

33. The method of claim 32 further including the step of operating said inlet pump at a reduced speed during said return cycle relative to pump speed during said draw cycle to reduce the return cycle volumetric flow rate while maintaining the interface position.

34. The method of claim 33 further including the steps of
providing a plasma collection bag connected to said separation vessel for receiving and holding plasma, and
operating valves associated with the plasma collection to collect plasma during said draw cycle only.

35. The method of claim 34 further including the step of establishing a target hematocrit level as a decreasing function of the blood processing rate.

36. The method of claim 35 wherein said hematocrit target level is determined by $C_1-C_2Q_{IN}$ where $Q_{IN}$ is the inlet flow and $C_1$ and $C_2$ are constants.

37. The method of claim 31 further including a start-up phase independent of said run phase, said start-up phase designed to rid the collection system of saline solution in a minimal period of time, said method including start-up steps comprising:
providing a waste bag connected to receive saline solution during a prime divert period,
sensing when blood arrives at the entry of said waste bag and thereupon ending said prime divert period and entering a succession of start-up draw and return cycles;
during said start-up return cycle, halting operation of said inlet pump thereby causing all blood accumulated in said storage bag to be returned to said donor thereby creating no recirculation flow.

38. The method of claim 31 wherein said sensing device monitors pressure in said return system and further including the step of indicating an empty storage bag by a precipitous drop in pressure.

39. A method of separating and collecting harvested blood components utilizing a centrifuge apparatus for separating blood components and one single lumen needle for insertion into a circulatory system of a donor, comprising:
beginning a draw cycle of a predetermined duration;
withdrawing whole blood from the circulatory system of the donor through the single lumen needle during the draw cycle;
delivering the whole blood to the centrifuge apparatus at a first substantially constant predetermined flow rate during said draw cycle;
centrifuging the whole blood in the centrifuge apparatus during the draw cycle to separate the whole blood into stratified layers stably positioned within said centrifuge apparatus, the stratified blood providing at least one harvested blood component and a remaining blood component;
storing the remaining blood component in a storage reservoir during the draw cycle;
ending the draw cycle at the end of the predetermined duration;
beginning a return cycle;

returning a first portion of the remaining blood component stored in the storage reservoir to the circulatory system of the donor during a return cycle;

recirculating a second portion of the remaining blood component from the return storage reservoir to the centrifuge apparatus at a second predetermined flow rate during the return cycle, said second rate substantially lower than said first rate while maintaining the stability of the interface position of the stratified layers;

centrifuging the second portion of the remaining blood component during the return cycle;

sensing when the storage reservoir is substantially empty; and ending the return cycle when the storage reservoir is substantially empty.

40. The method of claim 39 wherein:

the storage reservoir is a flexible bag held under pressure; and the sensing step is performed by sensing the pressure in the bag, low pressure being indicative of a substantially empty flexible bag.

41. The method of claim 39 wherein the remaining blood component contains a fraction of at the least one harvested blood component, and the step of centrifuging the second portion of the remaining blood component further comprises separating the second portion of the remaining blood component into a further quantity of the at least one harvested blood component and third portion of the remaining blood component and returning the third portion of the remaining blood component to the circulatory system of the donor.

42. The method of claim 39 wherein the ending of the draw cycle step is substantially simultaneous with the beginning of the return cycle step.

43. The method of claim 39 further comprising beginning a subsequent draw cycle wherein the ending of the return cycle step is substantially simultaneous with the beginning of the subsequent draw cycle step.

* * * * *

UNITED STATES PATENT AND TRADEMARK OFFICE
CERTIFICATE OF CORRECTION

PATENT NO. : 5,437,624
DATED : August 1, 1995
INVENTOR(S) : Robert W. Langley

It is certified that error appears in the above-indentified patent and that said Letters Patent is hereby corrected as shown below:

```
    Col. 5, line 5:   the word "be" should be --18--
```

In the Claims:
```
  Col. 12,
  Claim 19, line 1:   change "11" to --18--
  Col. 12
  Claim 23, line 1:   change "11" to --18--
  Col. 12
  Claim 26, line 1:   change "16" to --25--
  Col. 12
  Claim 27, line 1:   change "16" to --25--
```

Signed and Sealed this

Twelfth Day of December, 1995

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,437,624

DATED : August 1, 1995

INVENTOR(S) : Robert W. Langley

It is certified that error appears in the above-identified patent and that said Letters Patent is hereby corrected as shown below:

Column 16, claim 41, line 2, reverse the order of the words "at the" to read --the at--

Signed and Sealed this

Twenty-third Day of January, 1996

Attest:

BRUCE LEHMAN

*Attesting Officer*  *Commissioner of Patents and Trademarks*